US006709027B2

(12) United States Patent
Rittenhouse

(10) Patent No.: US 6,709,027 B2
(45) Date of Patent: Mar. 23, 2004

(54) CAPILLARY COLUMN SEALING TECHNIQUE

(75) Inventor: David Rittenhouse, Fair Oaks, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/791,332

(22) Filed: Feb. 23, 2001

(65) Prior Publication Data

US 2002/0117855 A1 Aug. 29, 2002

(51) Int. Cl.⁷ ................................................ F16L 21/06
(52) U.S. Cl. .................... 285/332; 604/283; 285/332.1; 285/115
(58) Field of Search ............................. 285/332.1, 332, 285/115, 123.15, 382; 604/283, 284

(56) References Cited

U.S. PATENT DOCUMENTS

| | | | |
|---|---|---|---|
| 823,944 A | | 6/1906 | Hart |
| 4,173,363 A | | 11/1979 | Stearns |
| 4,440,550 A | * | 4/1984 | Jenkins et al. ................ 95/89 |
| 4,792,396 A | | 12/1988 | Gundelfinger |
| 5,110,431 A | * | 5/1992 | Moring ........................ 204/451 |
| 5,234,235 A | * | 8/1993 | Worden ..................... 285/334.4 |
| 5,288,113 A | | 2/1994 | Silvis et al. |
| 5,480,380 A | * | 1/1996 | Martin ........................ 604/284 |
| 5,494,641 A | | 2/1996 | Krstanovic |
| 5,540,464 A | * | 7/1996 | Picha ........................... 285/332 |
| 5,578,157 A | * | 11/1996 | Higdon ........................ 285/332 |
| 5,601,785 A | * | 2/1997 | Higdon ....................... 210/198.2 |
| 5,611,846 A | | 3/1997 | Overton et al. |
| 5,653,885 A | * | 8/1997 | Jameson et al. ............ 210/149 |
| 5,749,604 A | * | 5/1998 | Williams .................... 285/382 |

FOREIGN PATENT DOCUMENTS

| | | |
|---|---|---|
| EP | 0698789 A1 | 2/1996 |
| JP | 2000-266270 | 9/2000 |

OTHER PUBLICATIONS

International Search Report dated Oct. 14, 2002 in connection with GB Application No.: 0204235.6 corresponding to U.S. application No. 09/791,332 in Great Britain.

* cited by examiner

Primary Examiner—Lynne H. Browne
Assistant Examiner—Aaron Dunwoody

(57) ABSTRACT

A method and apparatus for creating a fluid tight seal between a capillary column and a connector. The method and apparatus are easy to employ and do not require the use of screws, ferrules, or additional tools. The method can be used for any capillary tubing as well as for megabore and microbore columns and tubing. In the method, a length of auxiliary tubing is placed over the outside of tubing requiring a fluid tight seal, such as a capillary column. After the capillary column is inserted into the connector, the length of auxiliary tubing is press-fit into the connector creating a secondary fluid tight seal. The auxiliary tubing provides additional mechanical stability during mechanical vibration and dramatically increases the tensile force required to compromise the fluid seal. This method can be used for many types of chromatography including gas chromatography and liquid chromatography. A connector assembly and fluid tight seal assembly are also disclosed.

17 Claims, 3 Drawing Sheets

CAPILLARY COLUMN SEALING TECHNIQUE

TECHNICAL FIELD

The invention relates to capillary columns used to analyze chemical substances. More specifically, the invention is directed to a new method for creating a fluid tight seal between a capillary column and a connector.

BACKGROUND ART

Chromatographic apparatus used for both gas and liquid chromatography typically employ capillary columns to provide control passageways for substances to be analyzed. Areas of analytical application for capillary columns include gas chromatography, liquid microbore chromatography, capillary electrophoresis, and supercritical fluid chromatography. In most analytical applications today, glass, metal or flexible fused silica capillary columns are used. Occasionally, polymeric capillaries are also used. Frequently, it is necessary to join two pieces of capillary columns together in order to repair a broken column, to optimize a chemical separation by joining dissimilar columns, to extend the column length, or to add retention gaps or guard columns. In most analytical applications the column ends must also be connected to a sample injector and a detector.

Connectors are known in the art for receiving a fluid stream in a first fluid-bearing conduit and then delivering the received fluid stream to a second fluid-bearing conduit. In many cases, the fluid connection is obtained by manual manipulation of separate components that comprise the connector, such as by alignment and compression of a ferrule onto a column that is fitted to a receiving device.

The requirements placed upon a practical capillary connector for general use in chromatography applications are demanding. The connector must be able to withstand regular contact with chemically reactive substances and organic solvents. It must remain leak-free when operated at internal pressures ranging from zero (absolute) to several thousand pounds per square inch and over temperature cycles from sub-ambient to several hundred degrees Celsius. The thermal mass must be small and the thermal conductivity high to maintain thermal equilibrium between the column and its immediate surroundings. The dead volume in the joint must be as close to zero as possible Many connectors have been devised to address the need for providing a fluid tight coupling between column ends and connectors. Some connectors employ a ferrule with a conical frustrum exterior and a longitudinal bore. The column end is inserted through the bore of the ferrule and then the column-ferrule assembly is inserted into the interior of the connector. The interior of the connector is shaped to receive the ferrule. Pressure is then applied to the ferrule via a threaded fastener creating a fluid tight seal. Other connectors known as press-fit connectors consist of a hollow glass elongated tube having a conical configuration. Press-fit connectors have a tapered internal bore narrowing from the end to the central portion. In use a column end is inserted into the open end of the connector and moved into the press-fit position. Press-fit glass tubes have also been used with a ferrule and compression fitting at each end to seal against the capillary column. These methods are also used to connect the ends of two columns together with a fluid tight seal.

Known connectors provide low dead volume and chemically inert connections but suffer from several disadvantages. The ferrule and compression style connectors require several moving parts and require careful assembly. Many require separate elastomeric seals to ensure fluid-tight connection. The components used to make the seal must be chemically inert to the substances used in the analytical chromatographic process, and must exhibit good temperature stability. These components increase the cost and the complexity of the fluid seal and the connector. All of these connections show increased leakage at high temperatures, increased leakage after thermal cycling, and a sensitivity to tensions/torques applied to the fluid sealing location. The drawn conical connector of the press-fit variety has been reported to suffer from inconsistent fluid seal, particularly with modern high temperature fused silica capillary columns. At elevated temperature the fluid seal has been reported to leak and come apart.

SUMMARY OF THE INVENTION

Method and apparatus for establishing a fluid seal between capillary columns and connectors with a tapered conical internal bore is described. These methods and apparatus can be used when attaching the end of a column to an injectorport or a detector. The methods and apparatus can also be used when joining two capillary columns together end to end utilizing a union connector. In addition to establishing fluid tight seals for capillary tubing, these methods and apparatus can be used on a variety of tubular objects such as on larger bore tubing such as microbore columns, and megabore columns.

The improved fluid tight seal is generally accomplished by the following steps: 1) an auxiliary length of tubing is closely fit over the outside diameter of the capillary column so that a short length of the capillary column remains exposed; 2) the capillary column is press-fit into a connector with an internal conical taper shaped bore creating a fluid seal, and; 3) the auxiliary tubing is then moved into the connector and press-fit into the conical taper section of the connector creating a second fluid seal.

One of the advantages of these methods and apparatus is that it simplifies the installation of a column into a connector. The assembly of the auxiliary length of tubing is very simple and no additional screws, ferrules or tools are required to create a fluid tight seal. The outside diameter of the auxiliary tubing need not be bonded or glued into the internal bore of the connector nor does the outside diameter of the capillary column need to be glued or bonded to the inside of the auxiliary tubing. The capillary column and auxiliary tubing are press-fit into place to create a reliable fluid seal.

When assembled, the auxiliary tubing provides an extra seal that provides several operational benefits. The increase in the fluid sealing surface area increases the stability of the fluid seal during mechanical vibration. This in turn increases the tensile force required to compromise the fluid seal which dramatically reduces the leak rate of the fluid seal. Additionally, the auxiliary tubing adds essentially no physical and thermal mass, is reliable, and is inexpensive.

DETAILED DESCRIPTION OF THE INVENTION

A simple method and apparatus for establishing a fluid seal between tubing and a connecting device that has an internal conical tapered bore is described. The method and apparatus applies to, for example, capillary columns and capillary tubing, and other tubing including microbore and megabore columns and tubing. Throughout the specification, any reference to capillary columns applies to capillary tubing, microbore and megabore columns and tubing unless otherwise noted.

The method utilizes an auxiliary length of tubing to reinforce the fluid tight seal a capillary column and a connector. Initially, the auxiliary length of tubing is "closely fit" over a capillary column. Throughout this application the phrase "closely fit" indicates that the inner diameter of the auxiliary tubing has a length or is "dimensioned" so that the capillary column can be inserted through the auxiliary tubing yet there is contact between the outer surface of the capillary column and the inner surface of the auxiliary tubing. The closeness of the fit is such that the auxiliary tubing will remain in place over the outside of the capillary column when subjected to mechanical vibration.

The end of the capillary column is inserted through the auxiliary length of tubing leaving a length of capillary column exposed. The exposed length of capillary column is long enough so that the capillary column can be inserted and press-fit into the connector without the leading edge of auxiliary tubing making contact with the internal bore of the connector. The capillary column is press-fit into a connector which has an internal conical tapered bore creating a first fluid tight seal. Subsequently, the auxiliary length of tubing is press-fit into the connector creating a second fluid tight seal.

The force during assembly deforms the auxiliary tubing such that a fluid seal is made between the leading edge of the auxiliary tubing and the taper bore of the connector. The force also presses the auxiliary tubing tight to the capillary column, creating a fluid seal between the auxiliary tubing and the capillary column. Both the first fluid seal made with the capillary tubing and the second fluid seal made with the auxiliary length of tubing are established in the internal conical tapered bore section of the connector or fitting.

Figure 1A:
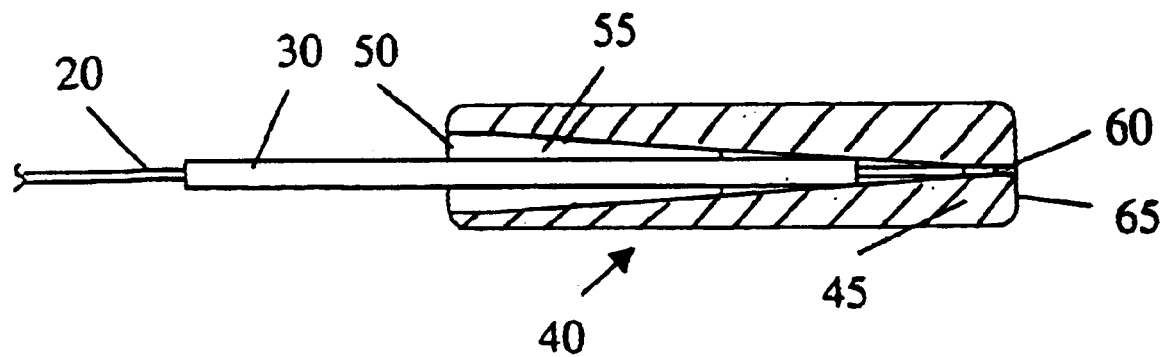
FIGS. 1A and 1B each illustrate a single connector.

FIG. 1A illustrates a sectional view of one embodiment for capillary columns. FIG. 1A shows an improved fluid tight seal consistent with this invention and accomplished by the following steps: 1) an auxiliary length of tubing 30 is closely fit over the outside diameter of a capillary column 20 so that a length of the capillary column 20 remains exposed; 2) the capillary column 20 is press-fit into a connector 40 having an internal conical taper shaped bore 55; and 3) the auxiliary tubing 30 is then moved into the connector 40 and press-fit into the conical taper shaped bore 55.

The connector 40 includes a body 45 that has a flared entry 50 at one end. The flared entry 50 narrows into a tapered conical internal bore 55. The internal bore 55 tapers to a portion 60 that has an essentially consistent diameter, which terminates at the end 65 of the body 45 of the connector 40. The body 45 is preferably fabricated of ceramic, glass, metal such as stainless steel, or polymeric materials such as PEEK. Other materials may be used so long as they are able to withstand the conditions the connector will be exposed to. The flared entry 50 has a diameter that is wide enough to facilitate insertion of the capillary column 20 and the auxiliary length of tubing 30. The tapered conical internal bore 55 is dimensioned so that a friction fit is created between the wall of the tapered conical internal bore 55 and the outer diameter of the inserted end of both the capillary column 20 and auxiliary tubing 30. The internal bore 55 extends the length of the body 45 of the connector 40 and subtends at an angle that is approximately 2 degrees. However, this is only illustrative; the length, angle, and diameter of the tapered conical bore may vary according to the type of connector being used. Examples include connectors used for microbore and megabore tubing. The diameter of the portion 60 that has an essentially consistent diameter may also vary according to the type of connector used, but it is smaller than the diameter of the capillary column 20.

The capillary column 20 is any capillary tubing including those used as columns for gas and liquid chromatography. Additionally the method of this invention encompasses tubing of larger diameter than capillary tubing. Examples of larger diameter tubing include microbore and megabore tubing.

The auxiliary length of tubing 30 is preferably formed from polyimide, but could be formed of other material and is limited only by chemical and mechanical compatibility, and intended temperature range of the seal. The internal diameter of the auxiliary length of tubing 30 and the outer diameter of the capillary column 20 have a ratio from 1/1 to 2/1. Preferably, the auxiliary tubing 30 has an internal diameter such that the capillary column 20 can be inserted into the auxiliary tubing yet the inside surface of the auxiliary tubing 30 is in contact with the outside surface of the capillary column 20. The auxiliary tubing 30 has an outer diameter such that it can be press fit into the internal bore 55.

Figure 5:
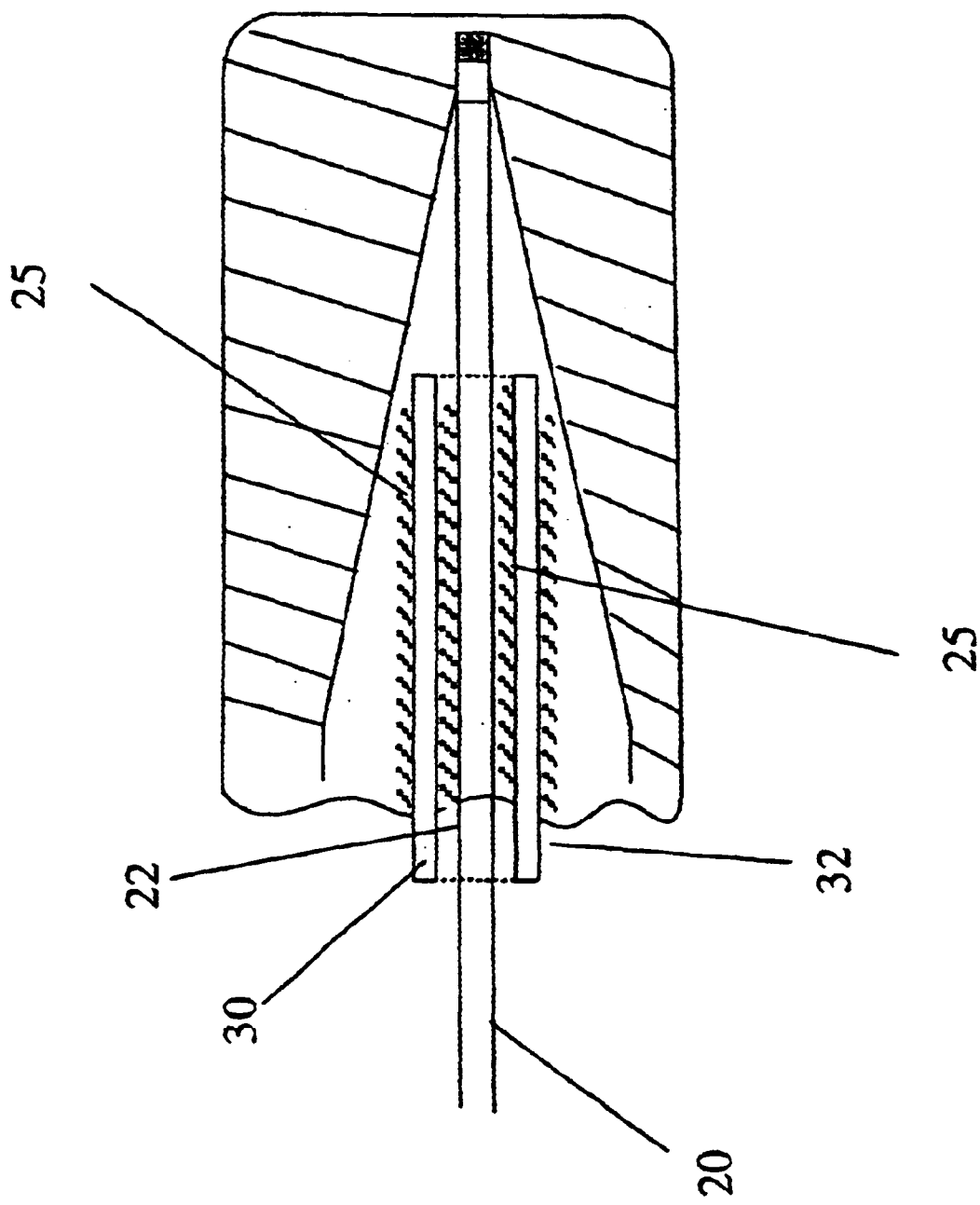
FIG. 5 depicts a single connector illustrating the addition of a bonding agent.

The outside surface of the auxiliary length of tubing 30 does not require any glue or bonding agents to create the second or secondary fluid tight seal. However, in one embodiment of the invention, the addition of a suitable bonding agent is utilized. As illustrated in FIG. 5, the bonding agent 25 is applied to the outer surface 22 of the capillary column 20 before the auxiliary length of tubing 30 is closely fit over the capillary column 20. Alternatively, the bonding agent 25 may be applied over the outer surface 32 of the auxiliary tubing 30 prior to being press fit into the connector 40. The addition of a bonding agent 25 will increase the strength of the fluid seal and mechanical integrity of the connection. The choice of bonding agents is limited by chemical compatibility with the tubing material, the intended temperature range, and the thermal cycling of the application. A preferred bonding agent is a polyimide resin. In yet another embodiment, the auxiliary length of tubing is constructed of partially cured material that is the same material as the capillary column 20 coating material. This method of attachment will cause the auxiliary length of tubing 30 and the capillary column 20 to cure and bond together without the addition of a bonding agent when subjected to elevated temperatures. This method also can further increase the mechanical integrity of the connection between the capillary column 20 and the auxiliary tubing 30.

Figure 1B:
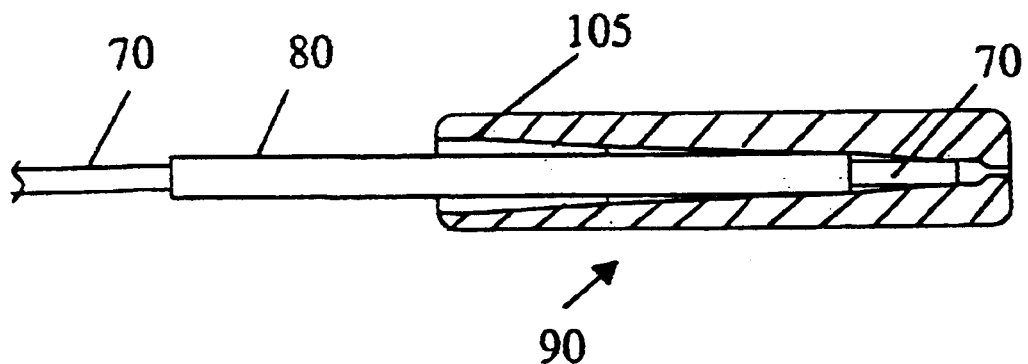
Figure 2:
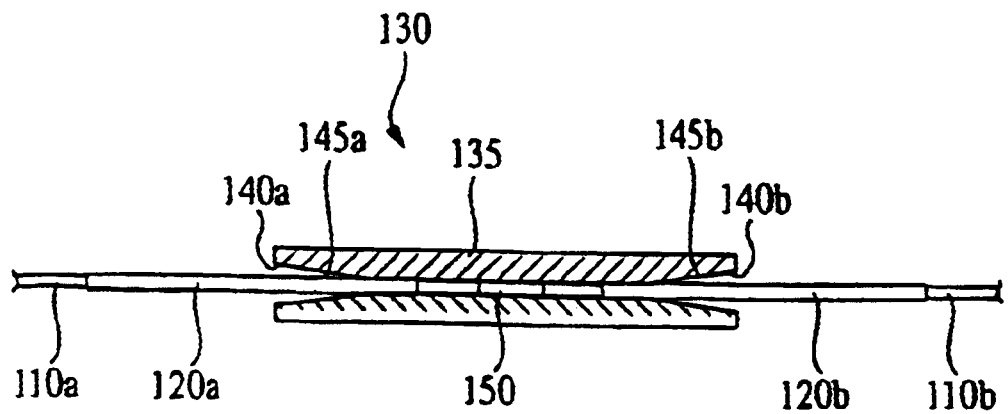
FIG. 2 depicts a press-fit glass union.
Figure 3:
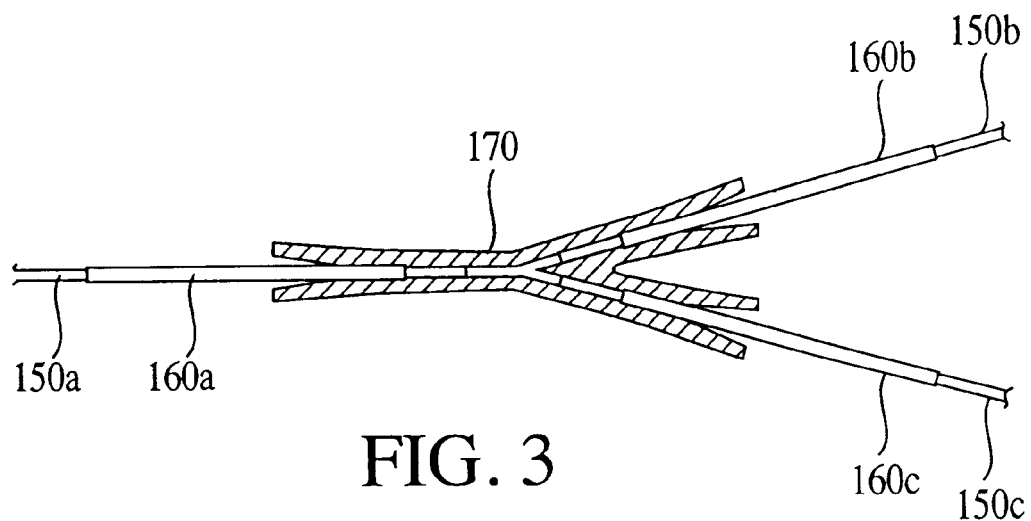
FIG. 3 depicts a three-way glass union.

FIGS. 1B, 2, and 3 illustrate other embodiments. In general, the discussion of the components in FIG. 1A applies to FIGS. 1B, 2, and 3.

FIG. 1B illustrates a sectional view of another embodiment. The components are essentially the same as in FIG. 1A except that the capillary column 20 of FIG. 1A is substituted with a megabore column 70. The megabore connector 90 is designed essentially the same as the connector 40 in FIG. 1A except that it is sized to receive a megabore column.

The auxiliary length of tubing 80 is closely fit over the outside diameter of the megabore column 70. The megabore column 70 is inserted into the megabore connector 90 and press-fit into internal conical bore 105. The auxiliary length of tubing 80 is then press-fit into the internal bore 105.

FIG. 2 illustrates the sectional view of another embodiment. FIG. 2 shows two individual capillary columns 110a and 110b each with an auxiliary length of tubing 120a and 120b closely fit over the outside diameter of the capillary columns 110a and 110b. The capillary columns 110a and 110b and the auxiliary lengths of tubing 120a and 120b are press-fit into a union connector 130.

The union connector 130, a press-fit union design, includes a body 135 that has flared entries 140a and 140b at both ends. Flared entries 140a and 140b narrow into tapered conical internal bores 145a and 145b. The internal bores 145a and 145b taper to a portion 150 of internal bore that has an essentially consistent diameter. The portion 150 of internal bore has a diameter that is smaller than the diameter of either capillary column 110a or 110b. The connector is a press fit glass union but other union designs can be used. The only required feature of a union used in this invention is that the internal bores 145a and 145b are dimensioned so that both the capillary tubes 110a and 110b and the auxiliary lengths of tubing 120a and 120b can be inserted and press-fit into the internal bores 145a and 145b.

The capillary columns 110a and 110b can be any capillary tubing; they can be identical capillary columns or different ones depending on the intended use. The capillary columns 110a and 110b can also be tubing of a larger diameter such as microbore or megabore.

The auxiliary lengths of tubing 120a and 120b operate as they do in FIGS. 1A and 1B. The internal bore of the auxiliary lengths of tubing 120a and 120b and the outside diameter of the capillary columns 110a and 110b are dimensioned so that a close fit is created between the capillary columns 110a and 110b and the auxiliary lengths of tubing 120a and 120b. The outside diameter of the auxiliary lengths of tubing 120a and 120b are dimensioned so that the auxiliary lengths of tubing 120a and 120b can be press-fit into internal bores 145a and 145b.

FIG. 3 illustrates the sectional view of another embodiment. FIG. 3 shows three individual capillary columns 150a, 150b, and 150c each with an auxiliary length of tubing 160a, 160b, and 160c closely fit over the outside diameter of the capillary columns 150a, 150b, and 150c. The capillary columns 150a, 150b, and 150c, and the auxiliary lengths of tubing 160a, 160b, and 160c, are press-fit into a 3-way press-fit union connector 170. The installation of the capillary columns 150a, 150b, and 150c are performed in the same way as in FIG. 2

Figure 4:
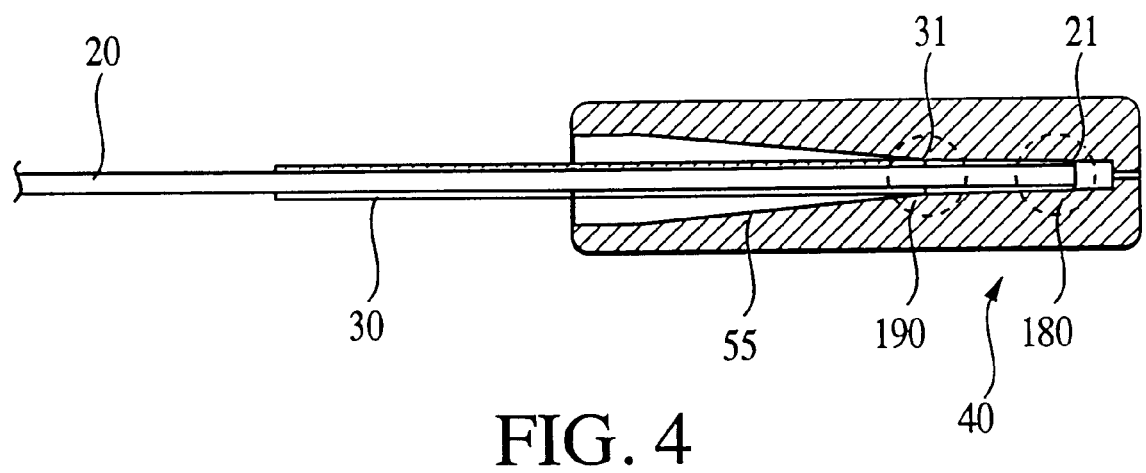
FIG. 4 depicts a single connector illustrating primary and secondary fluid seals.

FIG. 4 illustrates an enlarged sectional view of a single connector incorporating the invention. FIG. 4 illustrates the primary and secondary fluid seal of the invention. The components are the same as in FIG. 1A. The capillary column 20 is press-fit into the connector 40 creating the first or primary fluid tight seal 180. The auxiliary length of tubing 30 is subsequently press fit into the connector 40 creating the second or secondary fluid tight seal 190. Both seals are typically present in each of the embodiments shown in FIGS. 1A, 1B, 2, and 3.

Usually, the force during assembly deforms the capillary column 20 so that a fluid seal is made between the leading edge 21 of the capillary column 20 and the tapered conical internal bore 55 section of the connector 40. Additionally the force during assembly usually deforms the auxiliary length of tubing 30 so that a fluid seal is made between the leading edge 31 of the auxiliary length of tubing 30 and the tapered conical internal bore 55 section of the connector 40. The force also presses the auxiliary length of tubing 30 tight to the outside surface of the capillary column 20 creating a fluid seal between the inside surface of the auxiliary length of tubing 30 eliminating a fluid flow path between the capillary column 20 and the auxiliary length of tubing 30. Alternatively, any of the aforementioned seals may be made by a friction fit. The resulting connection has improved mechanical stability with minimal dead volume that is simple to install.

What is claimed is:

1. A method for establishing a fluid seal between a capillary column and a connector comprising the following steps:
   (i) inserting a capillary column through a length of cylindrical auxiliary tubing leaving a portion of the capillary column exposed;
   (ii) press-fitting the capillary column into a connector with a conical tapered bore creating a first fluid seal between the exposed portion and the connector; and
   (iii) moving the auxiliary tubing into the connector with the conical tapered bore and press fitting the auxiliary tubing into the connector creating a second fluid seal between a leading edge of the auxiliary tubing and the conical tapered bore of the connector.

2. The method of claim 1, further comprising applying a bonding agent to the outside of the auxiliary tubing prior to step (iii).

3. The method of claim 1, wherein step (i) inserts the capillary column through a length of partially cured cylindrical auxiliary tubing.

4. The method of claim 1, wherein step (ii) press-fits the capillary column into a connector that is a press-fit union design or a 3 way press-fit union design.

5. The method of claim 1, further comprising dimensioning the connector and auxiliary tubing to accommodate a megabore column.

6. The method of claim 1, further comprising dimensioning the connector and auxiliary tubing to accommodate a microbore column.

7. The method of claim 1 wherein the capillary column is capillary tubing.

8. The method of claim 5 wherein the megabore column is megabore tubing.

9. The method of claim 6 wherein the microbore column is microbore tubing.

10. The method of claim 1, further comprising using the capillary column and the connector for gas chromatography or liquid chromatography.

11. A fluid tight seal assembly comprising:
    a connector having a conical tapered bore;
    a capillary column press fit into the connector forming a first fluid seal; and
    a cylindrical auxiliary tubing press fit into the connector, the cylindrical auxiliary tubing having an inner diameter dimensioned so that a close fit is created when the capillary column is inserted through the auxiliary tubing, and wherein the auxiliary tubing has an outer diameter dimensioned so that a second fluid seal is created when the auxiliary tubing is press-fit into the connector.

12. The fluid tight seal assembly of claim 11, further comprising a bonding agent applied to auxiliary tubing.

13. The fluid tight seal assembly of claim 11 wherein the auxiliary tubing comprises a partially cured material that cures and bonds together with the capillary column when subjected to a particular temperature.

14. The fluid tight seal assembly of claim 11 wherein the capillary column comprises a megabore column and the auxiliary tubing has an inner diameter dimensioned to accommodate the megabore column.

15. The fluid tight seal assembly of claim 11 wherein the capillary column comprises a microbore column and the auxiliary tubing has an inner diameter dimensioned to accommodate the microbore column.

16. A method for establishing a fluid seal between a capillary column and a connector comprising the following steps:

(i) inserting a capillary column through a length of cylindrical auxiliary tubing leaving a portion of the capillary column exposed;

(ii) press-fitting the capillary column into a connector with a conical tapered bore creating a first fluid seal between the exposed portion and the connector; and (iii) moving the auxiliary tubing into the connector with the conical tapered bore and press fitting the auxiliary tubing into the connector creating a second fluid seal between the auxiliary tubing and the connector and a third fluid seal between the auxiliary tubing and the capillary column.

17. The method of claim 16 wherein the press fitting the auxiliary tubing step creates the second fluid seal in the conical tapered bore of the connector.

* * * * *